United States Patent
Cannell et al.

(10) Patent No.: US 6,558,697 B2
(45) Date of Patent: *May 6, 2003

(54) COMPOSITIONS AND METHODS FOR TREATING HAIR AND SKIN USING AQUEOUS DELIVERY SYSTEMS

(75) Inventors: David W. Cannell, New York, NY (US); Hitrendra Mathur, Woodbridge, NJ (US); Nghi Nguyen, Edison, NJ (US); Cynthia Espino, Princeton, NJ (US)

(73) Assignee: L'Oreal, Paris (FR)

(*) Notice: Subject to any disclaimer, the term of this patent is extended or adjusted under 35 U.S.C. 154(b) by 0 days.

This patent is subject to a terminal disclaimer.

(21) Appl. No.: 09/934,469

(22) Filed: Aug. 23, 2001

(65) Prior Publication Data

US 2002/0012647 A1 Jan. 31, 2002

Related U.S. Application Data

(63) Continuation of application No. 09/207,656, filed on Dec. 9, 1998.

(51) Int. Cl.$^7$ ............... A61K 9/127; A61K 7/06; A61K 9/107
(52) U.S. Cl. ............... 424/450; 424/401; 424/47; 424/70.1; 424/70.2; 424/70.11; 424/70.21; 424/70.22; 424/73; 514/880; 514/881; 514/937
(58) Field of Search ............... 424/401, 450, 424/70.1, 70.2, 70.11, 70.21, 70.22, 73; 43–47; 514/880, 881, 937

(56) References Cited

U.S. PATENT DOCUMENTS

| 3,996,146 A | 12/1976 | Tarasov et al. |
|---|---|---|
| 4,174,296 A | 11/1979 | Kass |
| 4,874,553 A | 10/1989 | Hager et al. |
| 5,002,761 A | 3/1991 | Mueller et al. |
| 5,160,739 A | 11/1992 | Kanga ............... 424/401 |
| 5,173,303 A | 12/1992 | Lau et al. |
| 5,672,350 A | 9/1997 | Tabibi ............... 424/450 |
| 5,783,554 A | 7/1998 | Li ............... 510/488 |
| 5,804,203 A | 9/1998 | Hahn ............... 424/401 |
| 6,015,574 A | 1/2000 | Cannell et al. |

FOREIGN PATENT DOCUMENTS

| BE | 895 719 A1 | 7/1983 |
|---|---|---|
| EP | 123 071 A2 | 10/1984 |
| EP | 340 592 A2 | 11/1989 |
| EP | 0 521 799 A1 | 1/1993 |
| EP | 0 868 898 A1 | 7/1998 |
| WO | WO 96/12469 | 5/1996 |
| WO | WO 96/28140 | 9/1996 |
| WO | WO 98/5633 | 12/1998 |

OTHER PUBLICATIONS

Ribosa et al., "Physico-chemical Modifications of Liposome Structures Through Interaction With Surfactants," *International Journal of Cosmetic Science*, pp. 131–149 (1992).
English Language Abstract of BE 895 719 A1.
International Search Report, dated Mar. 31, 2000.

*Primary Examiner*—Gollamudi S. Kishore
(74) *Attorney, Agent, or Firm*—Finnegan, Henderson, Farabow, Garrett & Dunner, L.L.P.

(57) ABSTRACT

Compositions containing at least one organic phospholipid capable of forming bilayers in aqueous solution; at least one amphoteric surfactant; and at least one nonionic surfactant present in an amount by weight equal to or greater than the amount of the phospholipid; where the phospholipid and surfactants are present in a combined amount sufficient to allow at least one water-insoluble ingredient selected from waxes and unneutralized and partially neutralized water-insoluble polymers, resins, and latexes to be incorporated into an aqueous solution. A delivery system containing the composition and methods for styling hair and for treating keratinous substances are also disclosed.

32 Claims, 2 Drawing Sheets

Figure 1:
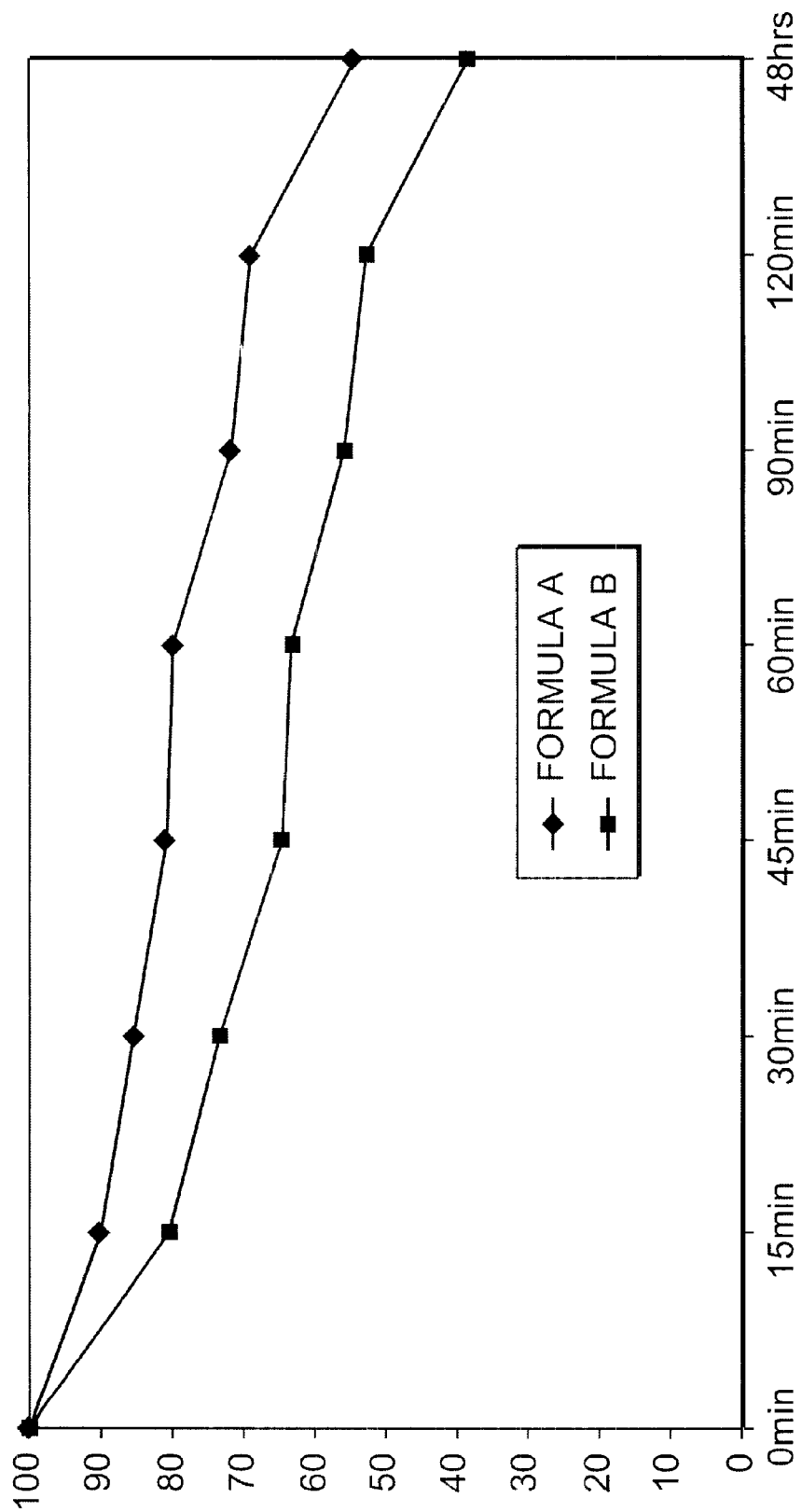

COMPOSITIONS AND METHODS FOR TREATING HAIR AND SKIN USING AQUEOUS DELIVERY SYSTEMS

This is a continuation of application Ser. No. 09/207,656, filed Dec. 9, 1998.

FIELD OF THE INVENTION

The present invention relates to compositions and delivery systems based on a combination of organic phospholipids capable of forming bilayers in aqueous solution; amphoteric surfactants; and nonionic surfactants, wherein the combination of these ingredients allows water-insoluble ingredients, particularly waxes or water-insoluble polymers, resins, or latexes, to be incorporated into aqueous solutions.

BACKGROUND OF THE INVENTION

Organic phospholipids play an important role in the cosmetics and pharmaceutical industries because of their outstanding physiological properties, such as, for example, emulsifying, softening, and anti-oxidant effects. When hydrolyzed, organic phospholipids yield phosphoric acid, an alcohol, a fatty acid, and a nitrogenous base. Most phospholipids are amphipathic, i.e., have polar "heads" and non-polar "tails." As a result, most phospholipids tend to arrange spontaneously into a bilayer when suspended in an aqueous environment, with the polar heads contacting the water and the non-polar tails contacting each other. Most naturally occurring phospholipids prefer to form vesicular bilayers in water solutions. In such a bilayer vesicle, no non-polar part of the phospholipid has any contact with the water solution.

Because of their non-polar portions, phospholipids typically are water-insoluble and incompatible with many water soluble anionic compounds, such as anionic surfactants. While they can be solubilized in water at low levels by a range of surfactants, this is often not easily accomplished.

Instead, solubilization has been accomplished conventionally using specific solubilizing agents in aqueous alcoholic solutions. For example, U.S. Pat. No. 4,874,553 to Hager et al. discusses methods of rendering phospholipid mixtures water-soluble or water-dispersible by using certain amine compounds as solubilizing agents. U.S. Pat. No. 4,174,296 to Kass describes a method of improving the solubility of phospholipid compounds in water, in particular lecithin compounds, by mixing lecithin with specific single solubilizing agents, including amphoteric and anionic surfactants. These methods require alcohol for cosolubilization. Alcohol solutions have the drawback of disrupting any bilayer formation by altering the solution such that the alcohol functions as a secondary solvent.

Lecithins and other phospholipids have been used in the pharmaceutical industry to formulate carriers for water-insoluble drugs. For instance, in U.S. Pat. No. 5,173,303 to Lau et al., water-insoluble material is encapsulated by vesicles composed of phospholipids such as lecithin. I. Ribosa et al., in "Physico-chemical modifications of liposome structures through interaction with surfactants," Int'l Journal of Cosmetic Science 14:131–149 (1992), also discuss solubilization of phospholipids via the interaction of liposomes with surfactants. Lau and Ribosa, however, investigated only dilute solutions of pure liposomes.

Despite difficulties in solubilization, certain organic phospholipids, such as lecithin, can advantageously give hair and skin a soft, moisturized feel because they have a strong affinity for the hydrophobic surface of the hair and skin. In addition, these phospholipids are toxicologically safe. It would thus be desirable for cosmetic and pharmaceutical applications to provide delivery systems that include such organic phospholipids as a carrier for other lipophilic ingredients, without the need for alcohols and other similar solvents.

In addition to solubilizing lipophilic ingredients such as oils, vitamins, and ceramides in aqueous systems, it would be desirable to solubilize other water-insoluble ingredients, such as waxes or unneutralized or partially neutralized polymers, resins, or latexes, in aqueous delivery systems. U.S. Pat. No. 5,391,368 to Gerstein teaches solubilization of a hair-styling polymer in a composition comprising an anionic surfactant and an amphoteric surfactant. According to Gerstein, it is the amphoteric surfactant which dissolves the water-insoluble styling polymer because the polymer is not soluble in the anionic surfactant alone.

Gerstein presents some problems, however. Many hair care and hair setting products are formulated at acidic pH because of a desire for such products to be compatible with the pH of the scalp and hair surface. Gerstein does not disclose a pH at which its system is formulated, but if the Gerstein system is acidified, the polymer will precipitate out of solution. In addition, the Gerstein system does not carry and there is no suggestion that it could carry any additional lipophilic ingredients in its mixture of anionic surfactant, amphoteric surfactant, and styling polymer. Further, Gerstein does not describe the incorporation of its styling polymer into any products other than the disclosed styling shampoo, nor does Gerstein suggest that such incorporation would be possible.

Thus, there remains a need for an aqueous delivery system that can solubilize water-insoluble materials in such a manner that they will not precipitate out of solution upon acidification and where the system could carry other ingredients in addition to the water-insoluble ingredient. There is additionally a need for hair styling products which contain reduced VOC (volatile organic content). Laws in several states have already set a ceiling for the acceptable percentage of VOC in consumer products. When, in an effort to lower VOC's, some of the alcohol used in such products is lowered and replaced with water, the product is unable to form a good film, is sticky and thick, and is generally an ineffective hair styling aid, resulting, for example, in unacceptable curls. Attempts to remedy the problems encountered when alcohol is replaced with water in these formulations have not resulted in satisfactory products either. In particular, although the amount of water-insoluble styling polymer or resin can be increased to improve the curl or styling capability of the hair product, the outcome is a tacky formulation which flakes easily on the hair. Alcohol can also be replaced with acetone instead of water, but, as is commonly known in the art, acetone is flammable and is also an undesirable ingredient in hair products because it is such a strong solvent and can, for example, dissolve many varnishes or finishes. For instance, if a user is spraying the product on the hair while wearing nail polish, the acetone content of the hair spray could cause the nail polish to dissolve and run from the hands into the hair.

Accordingly, there is a need for hair styling compositions with little or no volatile organic content which still effectively solubilize styling ingredients and hold the hair while still allowing the hair to be shiny, flexible, and washable.

SUMMARY OF THE INVENTION

In order to achieve these and other advantages, the present invention is drawn to a composition made up of at least one organic phospholipid capable of forming bilayers in aqueous solution; at least one amphoteric surfactant; and at least one nonionic surfactant. The nonionic surfactant is present in an amount by weight equal to or greater than the amount of the organic phospholipid. The phospholipid, amphoteric surfactant, and nonionic surfactant are present in a combined amount sufficient to allow at least one water-insoluble ingredient, selected from waxes and unneutralized and partially neutralized water-insoluble polymers, resins, and latexes, to be incorporated into an aqueous solution.

In another embodiment, the present invention relates to an aqueous delivery system for water-insoluble materials. As defined herein, "water-insoluble" means a material which is insoluble in water but which can be solubilized in accordance with the present invention. The delivery (or "carrier") system includes at least one organic phospholipid capable of forming bilayers in aqueous solution, at least one amphoteric surfactant, at least one nonionic surfactant, at least one water-insoluble ingredient selected from waxes and unneutralized and partially neutralized water-insoluble polymers, resins, and latexes, and an aqueous phase. The nonionic surfactant is present in an amount by weight equal to or greater than the amount of the organic phospholipid. The organic phospholipid, the amphoteric surfactant, and the nonionic surfactant are present in a combined amount sufficient to allow the water-insoluble ingredient to be incorporated into the delivery system.

The present invention is also drawn to a method for styling hair by preparing an aqueous solution comprising at least one organic phospholipid capable of forming bilayers in aqueous solution; at least one amphoteric surfactant; at least one nonionic surfactant present in an amount by weight equal to or greater than the amount of the at least one phospholipid; and at least one water-insoluble ingredient, selected from waxes and unneutralized and partially neutralized water-insoluble polymers, and latexes. The phospholipid and the two surfactants are present in a combined amount sufficient to allow the water-insoluble ingredient to be incorporated into the aqueous solution. The aqueous solution is then applied to the hair to improve styling and hold, and the hair is styled while still maintaining properties of flexibility, shine, and washability.

Finally, the present invention relates to a method for treating at least one keratinous substance by preparing an aqueous solution comprising at least one organic phospholipid capable of forming bilayers in aqueous solution; at least one amphoteric surfactant; at least one nonionic surfactant present in an amount by weight equal to or greater than the amount of the at least one phospholipid; and at least one water-insoluble ingredient, selected from waxes and unneutralized and partially neutralized water-insoluble polymers, resins, and latexes. The phospholipid and the two surfactants are present in a combined amount sufficient to allow the water-insoluble ingredient to be incorporated into the aqueous solution. The aqueous solution is then applied to the keratinous substance.

Reference will now be made in detail to the presently preferred embodiment(s) of the invention.

DETAILED DESCRIPTION OF THE PREFERRED EMBODIMENTS

Advantageously, the present invention allows otherwise water-insoluble materials or ingredients to be solubilized in an aqueous solution. No alcohol is required for cosolubilization, and there is no need for liposome preparation. As will be detailed herein, another advantage of the present invention is that, due to the use of partially neutralized or unneutralized polymers or resins, this residue can be easily rinsed off.

The composition of the invention is also easy to formulate and can be gentle on the hair when the surfactants used are generally mild. The inventive composition can also be used on the skin or eyelashes. Unlike the attempted solubilization of phospholipids in the prior art, the present invention requires the presence of at least one amphoteric surfactant and at least one nonionic surfactant in the concentrated solutions of phospholipid.

These compositions and delivery systems can be used in hair styling products such as mousses, sprays, gels, lotions, and creams, as well as in shampoos, conditioners, hair dyeing compositions, including oxidative dyes and bleaches, permanent waving compositions, curl relaxing compositions, hair setting compositions, bath and body products, sunscreens, or cosmetics such as mascaras and foundations.

These systems can also be used to deliver active water-insoluble pharmaceutical ingredients, particularly in topical applications. Such systems could further help protect against oxidation and rancidity by protecting sensitive ingredients in pharmaceuticals or foods.

Additionally, the "load" carried by these systems can be quite high, a benefit that inures both to the user and to the manufacturer in an economic sense. Load is defined as the weight of added hydrophobe (water-insoluble material) divided by the weight of the phospholipid expressed as a percentage. Thus, 1 g of hydrophobe in a composition with 5 g phospholipid is a ⅕ or 20% load. In the art, 50% is considered a high load and can be achieved with certain hydrophobes and surfactant combinations.

Without being bound to a particular theory, the inventors believe that in the composition of the present invention, an organized structure, likely a laminar gel, is formed between the organic phospholipid and the nonionic surfactant and is solubilized by the amphoteric surfactant. The organized structure can incorporate other water-insoluble materials or hydrophobes. In aqueous systems, the structure remains organized, as evidenced by the clarity of the solution, exhibiting a slight Tyndall light scattering effect, and, when concentrated, showing lamellar anisotropic structures under polarized light.

In one embodiment, therefore, the invention is drawn to a composition comprising at least one organic phospholipid capable of forming bilayers in aqueous solution, at least one amphoteric surfactant, at least one nonionic surfactant, where the nonionic surfactant is present in an amount by weight equal to or greater than the amount of the phospholipid and where the phospholipid and surfactants are present in a combined amount sufficient to allow at least one water-insoluble ingredient selected from waxes and unneutralized and partially neutralized water-insoluble polymers, resins, and latexes to be incorporated into an aqueous solution.

With respect to the ingredients of the inventive composition, the preferred organic phospholipids capable of forming bilayers in aqueous solution are lecithins. Lecithins are mixtures of phospholipids, i.e., of diglycerides of fatty acids linked to an ester of phosphoric acid. Preferably, lecithins are diglycerides of stearic, palmitic, and oleic acids linked to the choline ester of phosphoric acid. Lecithin is usually defined either as pure phosphatidyl cholines or as crude mixtures of phospholipids which include phosphatidyl choline, phosphatidyl serine, phosphatidyl ethanolamine, phosphatidyl inositol, other phospholipids, and a variety of other compounds such as fatty acids, triglycerides, sterols, carbohydrates, and glycolipids.

The lecithin used in the present invention may be present in the form of a liquid, powder, or granules. Lecithins useful in the invention include, but are not limited to, soy lecithin and hydroxylated lecithin. For example, ALCOLEC S is a fluid soy lecithin, ALCOLEC F 100 is a powder soy lecithin, and ALCOLEC Z3 is a hydroxylated lecithin, all of which are available from the American Lecithin Company.

Other than lecithins, another group of phospholipids which may be useful in the present invention are multifunctional biomimetic phospholipids. For example, the following multifunctional biomimetic phospholipids manufactured by Mona Industries may be useful: PHOSPHOLIPID PTC, PHOSPHOLIPID CDM, PHOSPHOLIPID SV, PHOSPHOLIPID GLA, and PHOSPHOLIPID EFA.

The amphoteric surfactants useful in the present invention include, but are not limited to, betaines, sultaines, hydroxysultaines, alkyl amphodiacetates, alkyl amphodipropionates, and imidazolines, or salts thereof. It is recognized that other fatty acid condensates such as those formed with amino acids, proteins, and the like are suitable. Amphoteric surfactants are typically available for commercial sale in solution form with the active surfactant accounting for approximately 40% of the total solution weight. Cocamphodipropionate is particularly preferred, for example, MIRANOL C2M-SF Conc. (disodium cocamphodipropionate), in its salt-free form, available from Rhône-Poulenc. MIRANOL is sold in solution form with amphoteric surfactants composing approximately 40% of the total solution weight; for example, 10 g of MIRANOL contain about 4 g of amphoteric surfactant. Also preferred is CROSULTAINE C-50 (cocamidopropyl hydroxysultaine), available from Croda. CROSULTAINE is also sold in solution form with the amphoteric surfactant composing approximately 50% of the total solution weight. Other amphoteric surfactants useful in the present invention include disodium wheatgermimido PEG-2 sulfosuccinate, available under the trade name MACKANATE WGD from McIntyre Group Ltd., which is a solution with amphoteric surfactants composing approximately 39% of the total solution weight, and disodium soyamphodiacetate, available under the trade name MACKAM 2S from McIntyre Group Ltd., which is a solution with amphoteric surfactants composing approximately 34.5% of the total solution weight.

The nonionic surfactants useful in the present invention are preferably formed from a fatty alcohol, a fatty acid, or a glyceride with a $C_8$ to $C_{24}$ carbon chain, preferably a $C_{12}$ to $C_{18}$ carbon chain, more preferably a $C_{16}$ to $C_{18}$ carbon chain, derivatized to yield a Hydrophilic-Lipophilic Balance (HLB) of at least 10. HLB is understood to mean the balance between the size and strength of the hydrophilic group and the size and strength of the lipophilic group of the surfactant. Such derivatives can be polymers such as ethoxylates, propoxylates, polyglucosides, polyglycerins, polylactates, polyglycolates, polysorbates, and others that would be apparent to one of ordinary skill in the art. Such derivatives may also be mixed polymers of the above, such as ethoxylate/propoxylate species, where the total HLB is preferably greater than or equal to 10. Preferably the nonionic surfactants contain ethoxylate in a molar content of from 10–25, more preferably from 10–20 moles.

Nonionic surfactants may be selected from, but are not limited to, the following:

| # of Cs | Name | Trade Name |
|---|---|---|
| C-12 | Laureth-23 | BRIJ 35, available from ICI Surfactants |
| C-16 | Ceteth-10 | BRIJ 56, available from ICI Surfactants |
| C-16 | Ceteth-20 | BRIJ 58, available from ICI Surfactants |
| C-16 | IsoCeteth-20 | ARLASOLVE 200, available from ICI Surfactants |
| C-18 | Steareth-10 | VOLPO S-10, available from Croda Chemicals Ltd. |
| C-18 | Steareth-16 | SOLULAN-16, available from Amerchol Corp. |
| C-18 | Steareth-20 | BRIJ 78, available from ICI Surfactants |
| C-18 | Steareth-25 | SOLULAN-25, available from Amerchol Corp. |
| C-18 = | Oleth-10 | BRIJ 97, available from ICI Surfactants |
| C-18 = | Oleth-20 | VOLPO-20, available from Croda Chemicals Ltd. |

Alkyl polyglucose surfactants sold under the name PLANTAREN, available from Henkel, may also be used.

In one preferred embodiment of the composition of the present invention, the organic phospholipid capable of forming bilayers in aqueous solution, the amphoteric surfactant, and the nonionic surfactant are present in the composition such that the nonionic surfactant is present in an amount by weight greater than the amount of phospholipid. In a more preferred embodiment, the amount of phospholipid in the composition is kept fixed while the amounts of the amphoteric and nonionic surfactants are increased. Preferably, the phospholipid, amphoteric surfactant, and nonionic surfactant are present in a combined amount sufficient to allow at least one water-insoluble ingredient to be incorporated into an aqueous solution.

In a still more preferred embodiment, calculating the phospholipid as present at a value of 1, the phospholipid, amphoteric surfactant and nonionic surfactant are preferably present in the composition in a ratio ranging from about 1:1.2:2 and above, i.e., where the amounts of the surfactants can be increased independently of each other but the amount of phospholipid stays fixed. The ratio is considered to be "above" 1:1.2:2 when the amount of either of the surfactants increases. The ratio preferably ranges from about 1:2:2 to about 1:8:3. The loading capability for hydrophobes carried by the delivery system of the present invention is maximized if the ratio of nonionic surfactant to phospholipid is minimized, with the bilayers still being solubilized, because an excess of nonionic surfactant may disrupt the organized structure.

In general, the preferred compositions of the invention contain a lecithin (L), an amphoteric surfactant (A), and a nonionic surfactant (N), referred to as the "LAN." Although lecithin is particularly preferred, the types of amphoteric and nonionic surfactants may vary.

When used as an ingredient in further formulations, the LAN is compatible and generally gives clear solutions with anionic surfactants such as alkyl sulfates and ethoxylated alkyl sulfates. Other anionic surfactants such as sulfosuccinates may also be used. Typically, LAN compositions can resist storage at 45° C. for three months or more, which would predict that they have a shelf life at room temperature of at least three years.

In another aspect, the present invention relates to an aqueous delivery or carrier system comprising at least one organic phospholipid capable of forming bilayers in aqueous solution, at least one amphoteric surfactant, at least one nonionic surfactant preferably present in an amount greater than or equal to the amount of the phospholipid, at least one water-insoluble ingredient selected from waxes and unneutralized and partially neutralized water-insoluble polymers, resins, and latexes, and an aqueous phase. The phospholipid, amphoteric surfactant, and nonionic surfactant are present in a combined amount sufficient to allow the water-insoluble ingredient(s) to be incorporated into or solubilized by the aqueous system. The amount sufficient for solubilization may vary depending on the type of composition; for example, shampoo formulations require a lower concentration of LAN than do conditioner, deep treatment, bleach, permanent wave, dye, and relaxant compositions.

In the delivery system, the organic phospholipid, preferably lecithin, is preferably present in an amount greater than 0 to about 5% by weight of the delivery system as a whole. More preferably, the lecithin is present in an amount ranging from about 0.1 to about 0.3% by weight. Since lecithin itself is not a pure raw material and may have free glycerides, glycerin, fatty acids, and soaps, adjustments in this ratio may need to be made, i.e., one source of lecithin may require different ratios of nonionic and amphoteric surfactants than another to achieve maximum clarity of solution. Preferably, the composition of the invention forms a clear solution, though the purpose of the invention is achieved just as effectively with a slightly cloudy solution.

The amphoteric surfactant is preferably present in the delivery system in an amount ranging from greater than 0 to about 6%, more preferably from about 0.2 to 0.8%, by weight of the delivery system as a whole. The nonionic surfactant is preferably present in an amount of greater than 0 to about 20%, more preferably from about 0.3 to about 1% by weight relative to the weight of the delivery system as a whole.

Unneutralized and partially neutralized water-insoluble polymers and resins useful in the compositions or delivery systems of the present invention include, but are not limited to, those containing carboxyl moieties, such as acrylates and other carboxy polymers. Typically, water-insoluble polymers and resins have to be neutralized to about 90%–100% of their carboxyl moieties to make them water soluble for the purpose of formulating stable products in aqueous solution and for the purpose of making products which have good non-build-up properties, i.e., can be easily washed off the hair after use. Polymers which have a lower degree of neutralization are usually not water-soluble. Unneutralized or partially neutralized polymers can be solubilized with the help of organic solvents, e.g, in alcoholic or aqueous/alcoholic systems, but their ease or removal/washability from the hair or skin leaves a great deal to be desired.

When used with the compositions of the present invention, however, little or no neutralization is needed to dissolve these polymers/resins. The degree of neutralization is therefore from 0 to about 90% and preferably from about 55 to about 65%. In part, an unneutralized or partially neutralized water-insoluble polymer or resin is solubilized because it is neutralized by the amphoteric surfactant contained in the presently claimed delivery system, but the amphoteric surfactant acting alone will not solubilize the polymer or resin in water and allow the pH to be acidic. As discussed with reference to the Gerstein patent above, if the polymer or resin is neutralized by the amphoteric surfactant alone, when one attempts to acidify the solution to prepare a hair care composition with acidic pH, as is desirable, the carboxyl moieties of the polymer or resin becomes unneutralized and precipitation occurs. It is the combination of the organic phospholipid, the amphoteric surfactant, and the nonionic surfactant of the present invention which achieves the solubility of the water-insoluble polymers or resins.

Thus, one advantage of the present invention, particularly with respect to hair styling and treating products, is the ability of the LAN system to incorporate into an aqueous phase polymers or resins that are only partially neutralized. The LAN/partially neutralized polymer system is a stable, solvent-free, aqueous system that delivers the polymers onto hair or skin. This system is especially advantageous in providing products with a low VOC. As discussed above, the remedy for the problems encountered when water replaces alcohol in hair styling and treating compositions is to add more polymers/resins to improve the styling properties. However, this remedy has its own problems, in that a large amount of polymer may be needed and the result is a tacky, sticky composition which flakes. The LAN solves these difficulties by providing a system wherein a partially neutralized polymer or resin can be used for its styling properties but be present in a much lower amount than would be necessary in a non-LAN, low-VOC system. Accordingly, there is no problem of tackiness and the partially neutralized polymer provides much better curl and styling. Although unneutralized polymers are useful in the LAN compositions of the invention, partially neutralized polymers are preferred because they do not require as large an amount of LAN to be present in the delivery system. The effect of increased amounts of LAN is the enhancement of plasticizer properties in the composition. As a result, compositions with higher LAN do not hold a curl as well because the plasticizer properties tend to soften the hair.

Moreover, in spite of being partially neutralized, the polymers are as easy to remove from the hair as completely neutralized polymers. Partially neutralized or unneutralized polymers without the LAN would be difficult to remove from the hair since they are water-insoluble.

Another benefit of the LAN/partially neutralized polymer system over the completely neutralized polymer system is that the former displays a better curl retention at high humidity. Yet another benefit of this novel LAN system is that it imparts a soft, conditioning feel on hair (due to Lecithin) whereas the conventional completely neutralized polymer system requires the use of plasticizers to attain similar properties.

As for latexes, they generally have been used in cosmetics in an unneutralized form since they are used for their milky (insoluble) appearance. In the context of the present invention, however, water-insoluble latexes are neutralized and dissolved, producing a clear solution. To the best of the inventors' knowledge, neutralized latexes have not previously been used in cosmetic compositions.

The following are examples of polymers that can be incorporated into the deliver system of the present invention. The list is not intended to be limiting:

AMPHOMER LV-71 from National Starch (octylacrylamide/acrylates/butylaminoethyl methacrylate copolymer), OMNIREZ-2000 from ISP (PVM/MA half ethyl ester copolymer), RESYN 28-2930 from National Starch (Vinyl acetate/crotonates/vinyl neodecanoate copolymer), LUVIMER 100P from BASF (t-butyl acrylatelethyl acrylate/methacrylic acid), and ULTRAHOLD STRONG from BASF (acrylic acid/ethyl acrylate/t-butyl acrylamide).

Unneutralized or partially neutralized water-insoluble latexes have been used as film-formers in various applications. The following are latexes that can be incorporated into the delivery system of the present invention:

AMERHOLD DR-25 from Amerchol (acrylic acid/methacrylic acid/acrylates/methacrylates), LUVIMER 36D from BASF (ethyl acrylate/t-butyl acrylate/methacrylic acid), BALANCE CR from National Starch & Chemical (acrylate copolymer) and ACUDYNE 258 from Rohm & Haas (acrylic acid/methacrylic acid/acrylates/methacrylates/hydroxy ester acrylates).

Waxes can also be used as the water-insoluble ingredient in the present invention. The waxes preferably have melting points less than 45° C. Useful waxes include, but are not limited to, Dimethicone Copolyol and Dimethiconol Beeswax, available from Hanson Wax & Oils; BEESWAX WHITE SP 422P, available from Strahl and Pitsch; ULTRA-BEE WD, available from Hanson Wax & Oils; Tetradecanyl Octadecanyl Stearates and Behenates, Orange Wax, and Vegetable Diglycerides, all available from Kostner Keunen, Inc. Compositions and delivery systems of the present invention containing waxes as a water-insoluble ingredient are particularly useful in skin treatment, as well as hair treatment. The LAN/wax compositions can be used as moisturizers and to protect the skin, e.g., the scalp from irritation caused by chemical treatment or other sources.

The water-insoluble ingredient is present in the claimed invention in an amount of from about 1 to about 15% by weight on a dry basis, preferably from about 5 to about 8% by weight, relative to the total weight of the delivery system. If waxes are used as the water-insoluble ingredient, they are preferably present in an amount ranging up to about 2% by weight.

The aqueous phase of the inventive delivery system can contain additional ingredients such as anionic surfactants, organic salts, inorganic salts, proteins, hair dyes, water-soluble polymers, quaternary ammonium compounds, complex and simple carbohydrates, amino acids, preservatives and fragrances.

If the inventive system is to be used in concentrated form, i.e., with about 5% by weight of the organic phospholipid and 1% of added water-insoluble ingredient, the composition preferably has a pH ranging from 4–12 for maximum stability and clarity. The more concentrated the solution. the better the delivery.

If this blend is diluted with water or the blend is used as an ingredient in another composition, then the pH has a broader range, i.e., preferably ranges from 2–12, and a wider variety of additives can be included in the solution. When water is added to a concentrated LAN, it may appear to form a cloudy solution at first if a large amount of water is added at once. The LAN will eventually go into solution, however, and become clear or at least clearer. The time to clear decreases as the LAN ratio increases. Once the organized structure of the LAN forms, the addition of more water does not affect clarity. These dilute blends are still very effective in delivering water-insoluble ingredients. The blends can be freeze-dried to hygroscopic solids that redissolve into water. Encapsulation of such solids so that they do not pick up and retain excess moisture is also contemplated. Such encapsulated solids can have desirable storage properties and would be easy to dissolve into water at various dilutions. Understandably, the need for dilution varies depending on the water-insoluble material used.

In another embodiment, the present invention relates to a method for styling hair by preparing an aqueous solution comprising at least one organic phospholipid capable of forming bilayers in aqueous solution; at least one amphoteric surfactant; at least one nonionic surfactant present in an amount by weight equal to or greater than the amount of the phospholipid; and at least one water-insoluble ingredient selected from waxes and unneutralized and partially neutralized water-insoluble polymers, resins, and latexes. The phospholipid and surfactants are present in a combined amount sufficient to allow the water-insoluble ingredient to be incorporated into the aqueous solution. The aqueous solution is then applied to the hair to improve styling and hold, and the hair is then styled. The hair maintains properties of flexibility, shine, and washability. The aqueous solution applied to the hair may be in the form of a mousse, cream, gel, aerosol or non-aerosol spray, or lotion.

The present invention also relates to a method for treating keratinous substances such as the hair or skin by preparing an aqueous solution of LAN and waxes or water-insoluble polymers, resins, or latexes as described above and applying it to the keratinous substance. Treatments envisioned include, but are not limited to conditioning, moisturizing, or protecting, e.g., the scalp, from chemical treatment or other irritation.

Another embodiment of the present invention is drawn to a process for preparing the aqueous system of the present invention. This process comprises: (a) combining the at least one organic phospholipid, amphoteric surfactant, and noniornic surfactant as described above to obtain a mixture, (b) heating the mixture obtained in step (a), and (c) adding an aqueous solution to the heated mixture to obtain the desired carrier system. Water-insoluble ingredients may be added in step (a). Preferably the carrier system obtained can carry a high load (i.e., 50% is considered a high load) of the organic phospholipid/water-insoluble ingredient. The mixture is preferably heated at a temperature of 65° C. to 85° C., depending on the melting points of the solid surfactants.

More specifically, the preparation of the carrier system of the present invention may be carried out as follows. Lecithin (L) is dispersed in water. The water-insoluble material is combined with nonionic surfactant(s) (N) at appropriate ratios and added to the lecithin/water dispersion. An amphoteric surfactant (A) is added and the mixture is heated, preferably to a temperature of from 75° C. to 85° C. The combination of these ingredients results in a solution which is clear to slightly hazy and is referred to as the "LAN," which can then be used as a "raw material" to make finished products.

Alternatively, lecithin, amphoteric surfactant(s) and nonionic surfactant(s) can be weighed to appropriate ratios and heated to 70° C. with stirring. Water is then added q.s. at the same temperature. Another alternative method of preparation comprises adding the water-insoluble ingredient with mixing after solutions have cooled. This last alternative method helps protect heat-sensitive water-insoluble ingredients.

The resulting compositions may vary from clear to slightly hazy and are infinitely dilutable with water. The slight haze can be overcome by adjusting the ratio of lecithin to the surfactants, adjusting pH, or reducing concentrations of water-insoluble ingredients.

As mentioned previously, the composition and delivery system of the present invention can be used as an ingredient itself in, for example, shampoos, conditioners (rinse-off and leave-in), deep treatments for hair, body washes, bath gels, hair dyeing compositions, permanent wave formulations, relaxers, make-up preparations, particularly mascara and foundation, and skin creams or lotions. When the inventive compositions or delivery systems are used as shampoos, at least one anionic surfactant may also be included in the shampoo formulation, as it is a typical shampoo ingredient.

The LAN systems of the invention can be further associated, in hair products in particular, with proteins including hydrolyzed soy protein, lauryldimonium hydrolyzed soy protein (cationic Soya protein) and wheat amino acids. The proteins could also include corn, wheat, milk, or silk proteins, collagens, keratins, or others. Furthermore, taurine and arginine hydrochloride may be associated therein to maximize protein binding to the hair. Cationic proteins or proteins in general may be stabilizers for the LAN and enhance its delivery by changing the charge on the surface of the LAN structure. The skin and the hair attract cationic ingredients, and proteins are generally substantive to these tissues.

In conditioning emulsions, nonionic emulsifiers such as glyceryl stearate and PEG-100 stearate can be used, and the LAN may be treated as a water-insoluble ingredient itself.

The LAN may also include lipophilic ingredients such as silicones, oil-soluble vitamins such as Vitamin E and Vitamin A, sunscreens, ceramides and natural oils. The lipophilic ingredients may be in the form of sunscreens, bacteriostats, moisturizers, colors, topical pharmaceuticals and the like. Preferred lipophilic ingredients include: Vitamin E, Vitamin E Acetate, Vitamin A Palmitate, olive oil, mineral oil, 2-oleamido-1,3-octadecanediol, octylmethoxy cinnamate, octyl salicylate, and silicones such as dimethicone, cyclomethicone, phenyl trimethicone, dimethiconol, dimethicone copolyol, and laurylmethicone copolyol. The lipophilic ingredients will, for example, moisturize or condition the skin, hair, and/or eyelashes and leave behind no oily feel.

Other ingredients in the LAN hair care compositions may include cationic polymers, such as polyquaternium 4, polyquaternium 6, polyquaternium 7, polyquaternium 10, polyquaternium 11, polyquaternium 16, polyquaternium 22, and polyquaternium 32, cationic conditioners, such as quaternium 27, behenamidopropyl PG-dimonium chloride, hydroxyethyl tallowdimonium chloride, hexadimethrine chloride, stearalkonium chloride, and cetrimonium chloride, isoparaffins, sodium chloride, propylene glycol, preservatives such as phenoxyethanol, methylparaben, ethylparaben, and propylparaben, pH adjusters such as phosphoric acid, humectants such as trehalose, and emollients such as octyldodecanol. Many other examples of materials from the classes listed above would be readily known to one of ordinary skill in the art.

The invention will be further clarified by the following examples, which are intended to be illustrative of the invention, but not limiting thereof.

EXAMPLES

Example 1

The following non-aerosol hair sprays were formulated:

|  | Formula A partially (60%) neutralized | Formula B 100% neutralized |
|---|---|---|
| RESYN 28-2930* (water-insoluble polymer) | 5.00 | 5.00 |
| AMPHOMER LV-71* (water-insoluble polymer) | 1.07 | 1.07 |
| AMP (aminomethylpropanol) (neutralizer) | 0.45 | 0.75 |
| Alcohol SDA 40B | 55.00 | 55.00 |
| Vitamin E Acetate | 0.001 | 0.001 |
| Vitamin A Palmitate | 0.001 | 0.001 |
| HYDROTRITICUM WQ (protein) | 0.01 | 0.01 |
| UVINUL MS 40 (benzophenone-4) | 0.01 | 0.01 |
| Octyl Salicylate | 0.01 | 0.01 |
| DC Q25220 (plasticizer) | — | 0.54 |
| ALCOLEC F100 | 0.04 | — |
| MIRANOL C2M-SF | 0.40 | — |

-continued

|  | Formula A partially (60%) neutralized | Formula B 100% neutralized |
|---|---|---|
| ARLASOLVE 200 | 0.10 | — |
| Fragrance | 0.20 | 0.20 |
| Water (deionized) | 37.708 | 37.408 |

*From national Starch & Chemical (Bridgewater, NJ)

Formula A represents a LAN/60% neutralized polymer system and Formula B represents a 100% neutralized polymer system with an added plasticizer and no LAN. The ratio of the LAN used in Formula A is 1:4:2.5.

Curl resistance at high humidity is shown in FIG. 1. The data show that the curl efficiency of the LAN/partially neutralized polymer system outperformed the non-LAN/fully neutralized polymer system. There was no significant difference between the two formulas for wet and dry combing, flaking, and product removability comparisons.

Example 2

The following non-aerosol hair sprays were formulated:

|  | Formula 1 partially (60%) neutralized | Formula 2 100% neutralized |
|---|---|---|
| Balance CR* (water-insoluble polymer, 45% active) | 23.62 | 23.62 |
| AMP (used to neutralize polymer) | 0.90 | 1.42 |
| Alcohol | 55.00 | 55.00 |
| ALCOLEC F100 | 0.045 | — |
| MIRANOL C2M-SF | 0.225 | — |
| ARLASOLVE 200 | 0.135 | — |
| DC Q25220 (plasticizer) | — | 0.50 |
| Water | 20.07 | 19.46 |

*From national Starch & Chemical (Bridgewater, NJ)

Formula 1 represents a LAN (1:2:3)/60% neutralized polymer system and Formula 2 represents a 100% neutralized polymer system with a plasticizer. Balance CR, the water-insoluble polymer used in Formulas 1 and 2, is a milky, aqueous emulsion which the manufacturer recommends neutralizing to 100% for use. It is therefore not measured on a dry basis but still falls within the preferred ranges set forth above in the detailed description of the invention.

Figure 2:
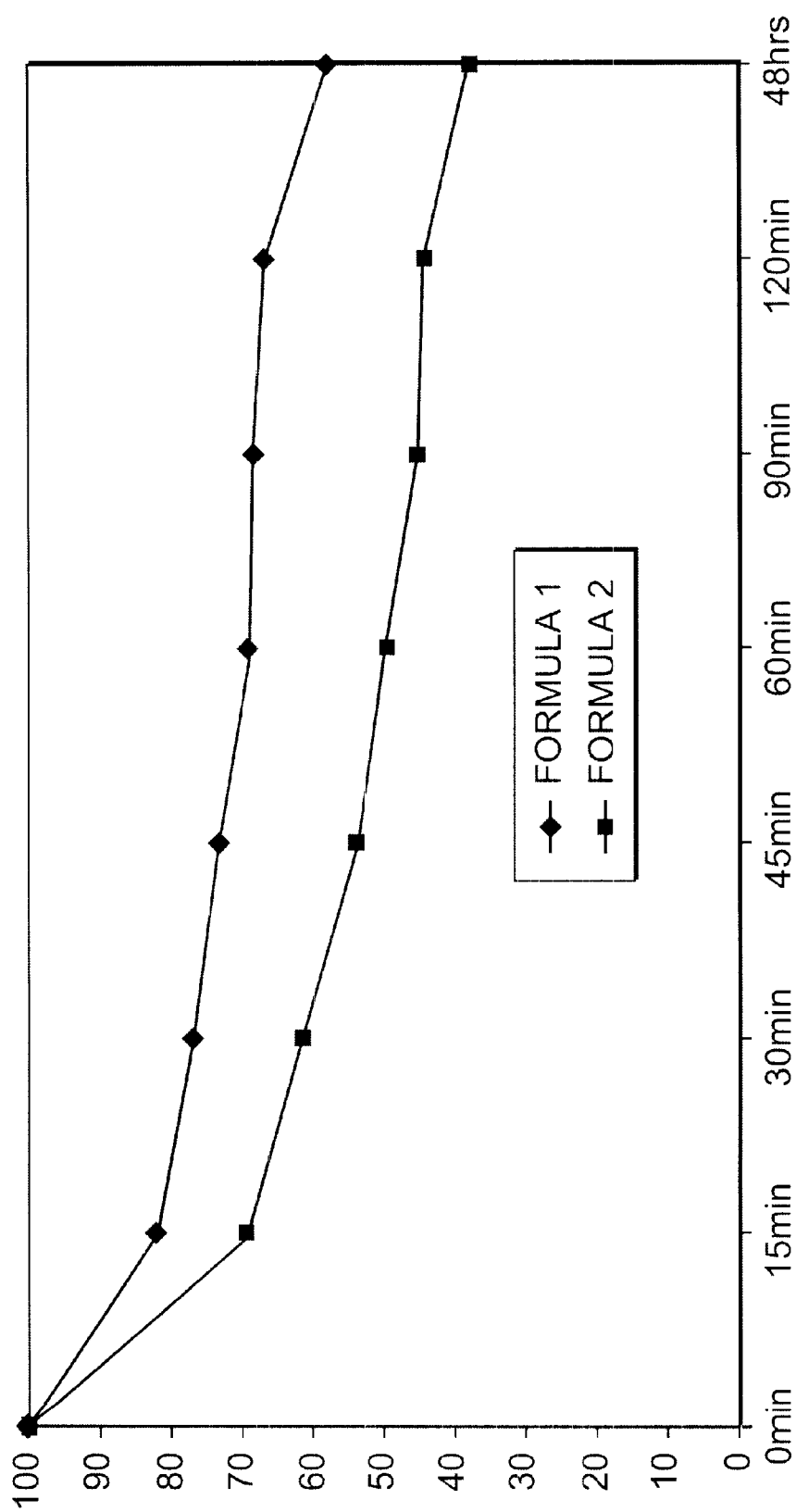

The test for the curl retention at high humidity (illustrated in FIG. 2) shows that the LAN/partially neutralized polymer system consistently had a better curl retention than the completely neutralized polymer system. Also, after four days of usage, at least 80% of the panelists rated both formulas as similar in manageability, wet and dry feel, and product removability.

Example 3

The following 55% VOC aerosol hairspray was prepared:

| Brand Name | CTFA Name | % w/w |
|---|---|---|
| Alcohol SDA 40B | Alcohol SDA 40B | 33.000 |
| AMP | Aminomethyl Propanol | 0.550 |
| ALCOLEC F 100 | Lecithin | 0.055 |
| MIRANOL C2 MSF | Disodium cocoamphodipropionate | 0.275 |

-continued

| Brand Name | CTFA Name | % w/w |
|---|---|---|
| ARLASOLVE 200 | Isoceteth 20 | 0.165 |
| Deionized water | Water | 14.555 |
| Vitamin E Acetate | Tocopheryl Acetate | 0.001 |
| Vitamin A Palmitate | Retinyl Palmitate | 0.001 |
| AMPHOMER LV 71 | Octylcrylamide/Acrylates Butylaminoethyl methacrylate copolymer | 2.310 |
| HYDROTRITICUM WQ | Hydroxypropyltrimonium hydrolyzed wheat protein | 0.006 |
| UVINUL MS 40 | Benzophenone-4 | 0.006 |
| Octyl Salicylate | Octyl Salicylate | 0.006 |
| Perfume oil | Fragrance | 0.165 |
| RESYN 28-2930 | VA/Crotonates/Vinyl Neodecanoate Copolymer | 3.905 |
| Dimethyl ether | Dimethyl ether | 25.700 |
| 1,1, difluoroethane | Hydroflurocarbon 152A | 19.300 |

Example 4

The following 55% VOC aerosol hairspray was prepared:

| Brand Name | CTFA Name | % w/w |
|---|---|---|
| Alcohol SDA 40B | Alcohol SDA 40B | 33.000 |
| AMP | Aminomethyl Propanol | 0.413 |
| ALCOLEC F 100 | Lecithin | 0.055 |
| MIRANOL C2 MSF | Disodium cocoamphodipropionate | 0.275 |
| ARLASOLVE 200 | Isoceteth 20 | 0.165 |
| Deionized water | Water | 15.104 |
| Vitamin E Acetate | Tocopheryl Acetate | 0.001 |
| Vitamin A Palmitate | Retinyl Palmitate | 0.001 |
| AMPHOMER LV 71 | Octylcrylamide/Acrylates Butylaminoethyl methacrylate copolymer | 0.605 |
| HYDROTRITICUM WQ | Hydroxypropyltrimonium hydrolyzed wheat protein | 0.006 |
| UVINUL MS 40 | Benzophenone-4 | 0.006 |
| Octyl Salicylate | Octyl Salicylate | 0.006 |
| Perfume oil | Fragrance | 0.028 |
| RESYN 28-2930 | VA/Crotonates/Vinyl Neodecanoate Copolymer | 5.335 |
| Dimethyl ether | Dimethyl ether | 25.700 |
| 1,1 Difluoroethane | Hydrofluorocarbon 152 A | 19.300 |

Example 5

The following quick-drying 55% VOC aerosol hairspray was prepared:

| Brand Name | CTFA Name | % w/w |
|---|---|---|
| Alcohol SDA 40B | Alcohol SDA 40B | 33.000 |
| AMP | Aminomethyl Propanol | 0.660 |
| ALCOLEC F 100 | Lecithin | 0.072 |
| MIRANOL C2 MSF | Disodium cocoamphodipropionate | 0.358 |
| ARLASOLVE 200 | Isoceteth 20 | 0.143 |
| Deionized water | Water | 15.742 |
| Vitamin E Acetate | Tocopheryl Acetate | 0.001 |
| Vitamin A Palmitate | Retinyl Palmitate | 0.001 |
| AMPHOMER LV 71 | Octylcrylamide/Acrylates Butylaminoethyl methacrylate copolymer | 4.950 |
| HYDROTRITICUM WQ | Hydroxypropyltrimonium hydrolyzed wheat protein | 0.006 |
| UVINUL MS 40 | Benzophenone-4 | 0.006 |
| Octyl Salicylate | Octyl Salicylate | 0.006 |
| Perfume oil | Fragrance | 0.055 |

-continued

| Brand Name | CTFA Name | % w/w |
|---|---|---|
| Dimethyl ether | Dimethyl ether | 25.700 |
| 1,1, difluoroethane | Hydrofluorocarbon 152 A | 19.300 |

Example 6

The following LAN (1:2:5) system containing ULTRABEE WD wax was prepared:

| | |
|---|---|
| ALCOLEC F100 | 5% |
| MIRANOL C2M-SF | 25% |
| ARLASOLVE 200 | 25% |
| ULTRABEE WD | 1% |
| WATER | 44% |

The resulting viscous, clear solution was indefinitely dilutable with water.

Example 7

The following LAN (1:1.6:4) system containing Deodorized Orange Wax was prepared:

| | |
|---|---|
| ALCOLEC F100 | 5% |
| MIRANOL C2M-SF | 20% |
| ARLASOLVE 200 | 20% |
| ULTRABEE WD | 2% |
| WATER | 53% |

The resulting viscous, clear orange solution was dilutable with water without any sign of precipitation.

It will be apparent to those skilled in the art that various modifications and variations can be made in the composition, delivery systems, and methods of the invention without departing from the spirit or scope of the invention. Thus, it is intended that the present invention cover the modifications and variations of this invention provided that they come within the scope of the appended claims and their equivalents.

What is claimed is:

1. A composition comprising:
    at least one phospholipid capable of forming bilayers in aqueous solution;
    at least one amphoteric surfactant;
    at least one nonionic surfactant present in an amount by weight equal to or greater than the amount of said at least one phospholipid; and
    at least one wax;
    wherein said at least one phospholipid, said at least one amphoteric surfactant, and said at least one nonionic surfactant are present in a combined amount sufficient to allow said at least one wax to be incorporated into an aqueous solution.

2. A composition according to claim 1, wherein said composition further comprises at least one anionic surfactant.

3. A composition according to claim 1, wherein said composition further comprises water.

4. A composition according to claim 1, wherein said at least one amphoteric surfactant is present in an amount by weight greater than the amount of said at least one phospholipid.

5. A composition according to claim 1, wherein said at least one nonionic surfactant is present in an amount by weight greater than the amount of said at least one phospholipid.

6. A composition according to claim 1, wherein said at least one phospholipid capable of forming bilayers in aqueous solution is a lecithin.

7. A composition according to claim 1, wherein said at least one amphoteric surfactant is selected from betaines, sultaines, hydroxysultaines, alkyl amphodiacetates, alkyl amphodipropionates, imidazolines, and salts thereof.

8. A composition according to claim 7, wherein said at least one amphoteric surfactant is cocamphodipropionate or cocamidopropyl hydroxysultaine.

9. A composition according to claim 1, wherein said at least one nonionic surfactant is formed from at least a $C_8$ to $C_{24}$ fatty alcohol, a $C_8$ to $C_{24}$ fatty acid, or a $C_8$ to $C_{24}$ glyceride.

10. A composition according to claim 1, wherein said at least one nonionic surfactant has an HLB of at least 10.

11. A composition according to claim 1, wherein said at least one phospholipid, said at least one amphoteric surfactant, and said at least one non ionic surfactant are present in a ratio of about 1:1.2:2 and above by weight.

12. A composition according to claim 11, wherein said at least one phospholipid, said at least one amphoteric surfactant, and said at least one nonionic surfactant are present in a ratio of about 1:2:2 to about 1:4.0:2 by weight.

13. A method for styling hair comprising:
preparing an aqueous solution comprising:
at least one phospholipid capable of forming bilayers in aqueous solution;
at least one amphoteric surfactant;
at least one nonionic surfactant present in an amount by weight equal to or greater than the amount of said at least one phospholipid; and
at least one water-insoluble ingredient selected from waxes and unneutralized and partially neutralized water-insoluble polymers, resins, and latexes,
wherein said at least one phospholipid, said at least one amphoteric surfactant, and said at least one nonionic surfactant are present in a combined amount sufficient to allow said at least one water-insoluble ingredient to be incorporated into said aqueous solution;
applying said aqueous solution to said hair to improve styling and hold;
styling said hair wherein said hair maintains properties of flexibility, shine, and washability.

14. A method according to claim 13, wherein said aqueous solution is in the form of a mousse, cream, gel, aerosol or non-aerosol spray, or lotion.

15. A delivery system for water-insoluble ingredients comprising:
at least one phospholipid capable of forming bilayers in aqueous solution;
at least one amphoteric surfactant;
at least one nonionic surfactant present in an amount by weight equal to or greater than the amount of said at least one phospholipid;
at least one wax; and
an aqueous phase,
wherein said at least one phospholipid, said at least one amphoteric surfactant, and said at least one nonionic surfactant are present in a combined amount sufficient to allow said at least one wax to be incorporated into said system.

16. A delivery system according to claim 15, wherein said aqueous phase further comprises additional ingredients selected from anionic surfactants, organic salts, inorganic salts, hair dyes, water-soluble polymers, amino acids, preservatives, and fragrances.

17. A delivery system according to claim 15, wherein said at least one phospholipid capable of forming bilayers in aqueous solution is a lecithin.

18. A delivery system according to claim 15, wherein said at least one amphoteric surfactant is selected from betaines, sultaines, hydroxysultaines, alkyl amphodiacetates, alkyl amphodipropionates, imidazolines, and salts thereof.

19. A delivery system according to claim 18, wherein said at least one amphoteric surfactant is cocamphodipropionate or cocamidopropyl hydroxysultaine.

20. A delivery system according to claim 15, wherein said at least one nonionic surfactant is formed from a $C_8$ to $C_{24}$ fatty alcohol, a $C_8$ to $C_{24}$ fatty acid, or a $C_8$ to $C_{24}$ glyceride.

21. A delivery system according to claim 15, wherein said at least one phospholipid is present in an amount of greater than 0 to about 5% by weight relative to the total weight of said delivery system.

22. A delivery system according to claim 15, wherein said at least one amphoteric surfactant is present in an amount of greater than 0 to about 15% by weight relative to the total weight of said delivery system.

23. A delivery system according to claim 15, wherein said at least one nonionic surfactant is present in an amount of greater than 0 to about 20% by weight relative to the total weight of said delivery system.

24. A delivery system according to claim 15, wherein said at least one wax is present in an amount of from about 1 to about 15% on a dry basis relative to the total weight of said delivery system.

25. A delivery system according to claim 15, wherein said at least one phospholipid, said at least one amphoteric surfactant, and said at least one nonionic surfactant are present in a ratio of about 1:1.2:2 and above by weight.

26. A delivery system according to claim 25, wherein said at least one phospholipid, said at least one amphoteric surfactant, and said at least one nonionic surfactant are present in a ratio of from about 1:2:2 to about 1:4:3 by weight.

27. A delivery system according to claim 15, wherein said system is in the form of a shampoo, a conditioner, a deep treatment for hair, a body wash, a bath gel, a bath oil, a hair dyeing composition, a permanent wave formulation, a make-up composition, a skin cream, or a lotion.

28. A method of delivering at least one water insoluble ingredient to at least one keratinous substance comprising:
preparing an aqueous solution comprising:
at least one phospholipid capable of forming bilayers in aqueous solution;
at least one amphoteric surfactant;
at least one nonionic surfactant present in an amount by weight equal to or greater than the amount of said at least one phospholipid; and
at least one wax,
wherein said at least one phospholipid, said at least one amphoteric surfactant, and said at least one nonionic surfactant are present in a combined amount sufficient to allow said at least one wax to be incorporated into said aqueous solution; and
applying said aqueous solution to said at least one keratinous substance.

29. A method according to claim 28, wherein said at least one keratinous substance is hair or skin.

30. A method according to claim 28, wherein said at least one keratinous substance is skin and wherein said applying further comprises conditioning, moisturizing, or protecting said skin from chemical treatment or skin irritation.

31. A delivery system according to claim 16, wherein said organic salts are chosen from quaternary ammonium compounds.

32. A delivery system according to claim 16, wherein said water-soluble polymers are chosen from proteins and complex and simple carbohydrates.

* * * * *

UNITED STATES PATENT AND TRADEMARK OFFICE
CERTIFICATE OF CORRECTION

PATENT NO. : 6,558,697 B2
DATED : May 6, 2003
INVENTOR(S) : David W. Cannell et al.

It is certified that error appears in the above-identified patent and that said Letters Patent is hereby corrected as shown below:

Column 15,
Line 22, "non ionic" should read -- nonionic --.

Column 17,
Lines 4-5, "chosen from quatermary ammonium compounds." should read
-- selected from at least one quaternary ammonium compound. --.

Column 18,
Line 2, "chosen" should read -- selected --.

Signed and Sealed this

Ninth Day of September, 2003

JAMES E. ROGAN
*Director of the United States Patent and Trademark Office*